US011000206B2

(12) United States Patent
Govari et al.

(10) Patent No.: US 11,000,206 B2
(45) Date of Patent: May 11, 2021

(54) ESOPHAGEAL PROBE WITH TRANSMITTING COILS

(71) Applicant: Biosense Webster (Israel) Ltd., Yokneam (IL)

(72) Inventors: Assaf Govari, Haifa (IL); Andres Claudio Altmann, Haifa (IL)

(73) Assignee: BIOSENSE WEBSTER (ISRAEL) LTD., Yokneam (IL)

( * ) Notice: Subject to any disclaimer, the term of this patent is extended or adjusted under 35 U.S.C. 154(b) by 307 days.

(21) Appl. No.: 15/794,287

(22) Filed: Oct. 26, 2017

(65) Prior Publication Data
US 2019/0125210 A1    May 2, 2019

(51) Int. Cl.
*A61B 5/06* (2006.01)
*A61B 18/14* (2006.01)
(Continued)

(52) U.S. Cl.
CPC ............... *A61B 5/062* (2013.01); *A61B 5/01* (2013.01); *A61B 5/6852* (2013.01); *A61B 8/12* (2013.01); *A61B 10/04* (2013.01); *A61B 18/1492* (2013.01); *A61B 34/20* (2016.02); *A61B 5/6853* (2013.01); *A61B 2017/00199* (2013.01); *A61B 2017/00243* (2013.01); *A61B 2017/00292* (2013.01); *A61B 2018/0022* (2013.01); *A61B 2018/00351* (2013.01); *A61B 2018/00357* (2013.01); *A61B 2018/00577* (2013.01); *A61B 2018/00642* (2013.01); *A61B 2018/00702* (2013.01); *A61B 2018/00761* (2013.01); *A61B 2018/00797* (2013.01);
(Continued)

(58) Field of Classification Search
CPC .......................... A61B 5/062; A61B 18/1492
USPC ........................................ 606/32, 33, 34, 41
See application file for complete search history.

(56) References Cited

U.S. PATENT DOCUMENTS

| 5,391,199 A | 2/1995 | Ben-Haim |
| 6,239,724 B1 | 5/2001 | Doron et al. |
| (Continued) | | |

FOREIGN PATENT DOCUMENTS

| EP | 2462891 A1 | 6/2012 |
| EP | 2737869 A1 | 6/2014 |
| (Continued) | | |

OTHER PUBLICATIONS

Extended European search report for corresponding European patent application No. EP 18202593.2, dated Mar. 6, 2019.

*Primary Examiner* — Linda C Dvorak
*Assistant Examiner* — Annabeth E Rodriguez
(74) *Attorney, Agent, or Firm* — Notaro, Michalos & Zaccaria P.C.

(57) ABSTRACT

A system for cardiac treatment includes a monitoring probe having a probe distal end, a magnetic field generator coupled to the probe distal end, a catheter having a catheter distal end, a magnetic sensor coupled to the catheter distal end, and a console. The monitoring probe is configured for insertion into an esophagus of a patient. The catheter is configured for insertion into a heart of a patient. The console is configured to drive the magnetic field generator to emit magnetic fields, to receive signals from the magnetic sensor in response to the magnetic fields, and to estimate respective distances between the catheter distal end and the probe distal end based on the signals.

20 Claims, 3 Drawing Sheets

(51) Int. Cl.
*A61B 5/00* (2006.01)
*A61B 18/00* (2006.01)
*A61B 5/01* (2006.01)
*A61B 34/20* (2016.01)
*A61B 8/12* (2006.01)
*A61B 10/04* (2006.01)
*A61B 90/00* (2016.01)
*A61B 17/00* (2006.01)

(52) U.S. Cl.
CPC ............... *A61B 2018/1467* (2013.01); *A61B 2034/2051* (2016.02); *A61B 2034/2072* (2016.02); *A61B 2090/3958* (2016.02); *A61B 2505/05* (2013.01); *A61B 2562/0223* (2013.01)

(56) References Cited

U.S. PATENT DOCUMENTS

| | | |
|---|---|---|
| 6,332,089 B1 | 12/2001 | Acker et al. |
| 6,484,118 B1 | 11/2002 | Govari |
| 6,593,884 B1 | 7/2003 | Gilboa et al. |
| 6,618,612 B1 | 9/2003 | Acker et al. |
| 6,690,963 B2 | 2/2004 | Ben-Haim et al. |
| 8,265,732 B2 | 9/2012 | Besz et al. |
| 8,271,095 B2 | 9/2012 | O'Sullivan |
| 8,355,801 B2 | 1/2013 | O'Sullivan |
| 2002/0065455 A1 | 5/2002 | Ben-Haim et al. |
| 2003/0120150 A1 | 6/2003 | Govari |
| 2004/0068178 A1 | 4/2004 | Govari |
| 2004/0254458 A1* | 12/2004 | Govari ............... A61B 8/12 600/437 |
| 2006/0106375 A1* | 5/2006 | Werneth ............ A61B 18/1492 606/32 |
| 2006/0116576 A1 | 6/2006 | McGee et al. |
| 2007/0106287 A1 | 5/2007 | O'Sullivan |
| 2007/0106289 A1 | 5/2007 | O'Sullivan |
| 2010/0030098 A1 | 2/2010 | Fojtik |
| 2010/0312096 A1* | 12/2010 | Guttman ............... A61B 5/415 600/411 |
| 2013/0006139 A1 | 1/2013 | Tiano |
| 2015/0141982 A1* | 5/2015 | Lee ..................... A61B 5/6858 606/41 |

FOREIGN PATENT DOCUMENTS

| | | |
|---|---|---|
| EP | 3090696 A1 | 11/2016 |
| WO | WO 96/05768 | 2/1996 |

\* cited by examiner

ESOPHAGEAL PROBE WITH TRANSMITTING COILS

FIELD OF THE INVENTION

The present invention relates generally to invasive medical devices and methods of treatment, and specifically to monitoring the position of an ablation probe within a living body.

BACKGROUND OF THE INVENTION

Systems for obtaining real-time spatial information on objects placed within a living body are often utilized for monitoring invasive treatments. For example, U.S. Pat. No. 9,131,853 describes a device that includes a probe adapted to be inserted into an esophagus of the patient. A first temperature sensor and a second temperature sensor are coupled to the probe. An electrode is also coupled to the probe. A controller generates a live and continuously updating three-dimensional anatomic map and three-dimensional thermal map of the esophagus during an ablation procedure based at least in part on the information received from the temperature sensors and the electrodes.

As another example, U.S. Pat. No. 6,593,884 describes a system and method for tracking the position and orientation of a probe. Three at least partly overlapping planar antennas are used to transmit electromagnetic radiation simultaneously, with the radiation transmitted by each antenna having its own spectrum. A receiver inside the probe includes sensors of the three components of the transmitted field. The position and orientation of the receiver relative to the antennas are determined noniteratively.

U.S. Pat. No. 8,617,152 describes devices, systems and methods for the ablation of tissue and treatment of cardiac arrhythmia. An ablation system includes an ablation catheter that has an array of ablation elements and a location element, an esophageal probe also including a location element, and an interface unit that provides energy to the ablation catheter. The distance between the location elements, determined by calculating means of the system, can be used by the system to set or modify one or more system parameter.

U.S. Pat. No. 8,355,801 describes a system and method for determining on a continuous, real-time basis the proximity of the esophagus to an endocardial catheter during mapping, ablation or other endocardial catheter-based procedures, comprising an esophagus probe catheter and an endocardial catheter adapted for proximal signal transmission between each other. A signal processing unit is included to process and compare a characteristic of the proximity signal that is changes or attenuates with distance between the two catheters, such as impedance, amplitude and/or phase. The system and method may include adaptations of the catheters with location sensor, and a mapping/navigational system for non-fluoroscopic location determination of the catheters.

U.S. Pat. No. 8,271,095 describes a system for determining the proximity of the esophagus to the ablation electrode of an ablation catheter during an ablation procedure. The system comprises an ablation catheter having at least one ablation electrode, an esophageal probe catheter having at least one electrode, and a signal processing unit. Both the ablation electrode and the esophageal probe catheter are electrically connected to the signal processing unit. The signal processing unit receives electrical signals from the ablation electrode on the ablation catheter and the electrode on the esophageal probe catheter and compares the signals to determine the proximity of the esophagus to the ablation electrode.

U.S. Patent Application Publication 2006/0116576 describes systems and method for navigating a medical probe (such as a catheter) relative to an anatomical body (such as a heart). A mark (such as a point or line), representing an anatomical region of interest (such as tissue targeted for treatment or tissue not targeted for treatment) is displayed on a representation of the anatomical body. The positions of the medical probe and the mark are determined within a three-dimensional coordinate system, and the proximity between the medical probe and the mark determined based on these positions.

U.S. Pat. No. 8,265,732 describes a method of catheter and radiating coil location in a human body and in particular to the determination over time of the location of the tip of a catheter as it is inserted and during its use in the body. In particular when a radiating coil is used in conjunction with a catheter, a coil locating device can be used to determine the distance the coil is from the device and hence its depth in the body of a patient. This is achieved by locating the coil-locating device on or over a predetermined landmark on the patient's body. U.S. Patent Application Publication 2010/0030098 describes a temperature probe for monitoring temperatures of a surface of a tissue or organ within the body of a subject includes a section with a substantially two-dimensional arrangement and a plurality of temperature sensors positioned across an area defined by the substantially two-dimensional arrangement. Such an apparatus may be used in conjunction with procedures are used to treat diseased tissue. Specifically, a temperature probe may be used to monitor temperatures across an area of a surface of a tissue or organ located close to the treated tissue to prevent subjection of the monitored tissue or organ to potentially damaging temperatures.

SUMMARY OF THE INVENTION

An embodiment of the present invention provides a system for cardiac treatment including a monitoring probe having a probe distal end, a magnetic field generator coupled to the probe distal end, a catheter having a catheter distal end, a magnetic sensor coupled to the catheter distal end, and a console. The monitoring probe is configured for insertion into an esophagus of a patient. The catheter is configured for insertion into a heart of a patient. The console is configured to drive the magnetic field generator to emit magnetic fields, to receive signals from the magnetic sensor in response to the magnetic fields, and to estimate respective distances between the catheter distal end and the probe distal end based on the signals.

In some embodiments, the system further includes one or more electrodes, which are disposed on the catheter distal end and are configured to apply electrical energy to ablate tissue in the heart, and the console is configured to estimate the respective distances between one or more of the electrodes and the probe distal end.

In some embodiments, the one or more electrodes include multiple electrodes disposed at respective locations around the catheter distal end, and the console is configured to estimate an orientation of the catheter distal end based on the signals, and to estimate the respective distances between the electrodes and the probe distal end responsively to the estimated orientation.

In some embodiments, the catheter distal end includes a balloon, which is inflatable within the heart, the one or more electrodes include multiple electrodes that are distributed around an outer surface of the balloon, and the console is configured to identify one of the electrodes that is closest to the esophagus responsively to a rotation angle of the balloon, which is indicated by the estimated orientation.

In an embodiment, the console is configured to limit an energy of ablation that is applied to the identified one of the electrodes.

In another embodiment, the catheter includes temperature sensors mounted in proximity to the electrodes, and the console is configured to control one or more ablation parameters responsively to a temperature indicated by one or more of the temperature sensors in proximity to the identified one of the electrodes.

In some embodiments, the console is configured to set different, respective ablation parameters for application of the electrical energy to the electrodes, responsively to the distances.

In an embodiment, the ablation parameters include at least one of a level of electrical power and a duration of the application of the electrical energy.

In an embodiment, the system further includes a needle, which is mounted on the catheter distal end and is configured to inject fluid or an implant. In another embodiment, the system further includes a biopsy tool, which is mounted on the catheter distal end and is configured to perform a biopsy. In some embodiments, the monitoring probe includes an ultrasound transducer configured to generate and detect echo signals.

There is additionally provided, in accordance with an embodiment of the present invention, a method for cardiac treatment including inserting a monitoring probe, which includes a probe distal end having a magnetic field generator coupled thereto, into an esophagus of a patient. A catheter, which includes a catheter distal end having a magnetic sensor coupled thereto, is inserted into a heart of the patient. The magnetic field generator is driven to emit magnetic fields while the probe distal end is in the esophagus. Respective distances between the catheter distal end and the probe distal end are estimated based on signals received from the magnetic sensor in response to the magnetic fields while the catheter distal end is in the heart.

The present invention will be more fully understood from the following detailed description of the embodiments thereof, taken together with the drawings in which:

DETAILED DESCRIPTION OF EMBODIMENTS

Overview

Figure 1:
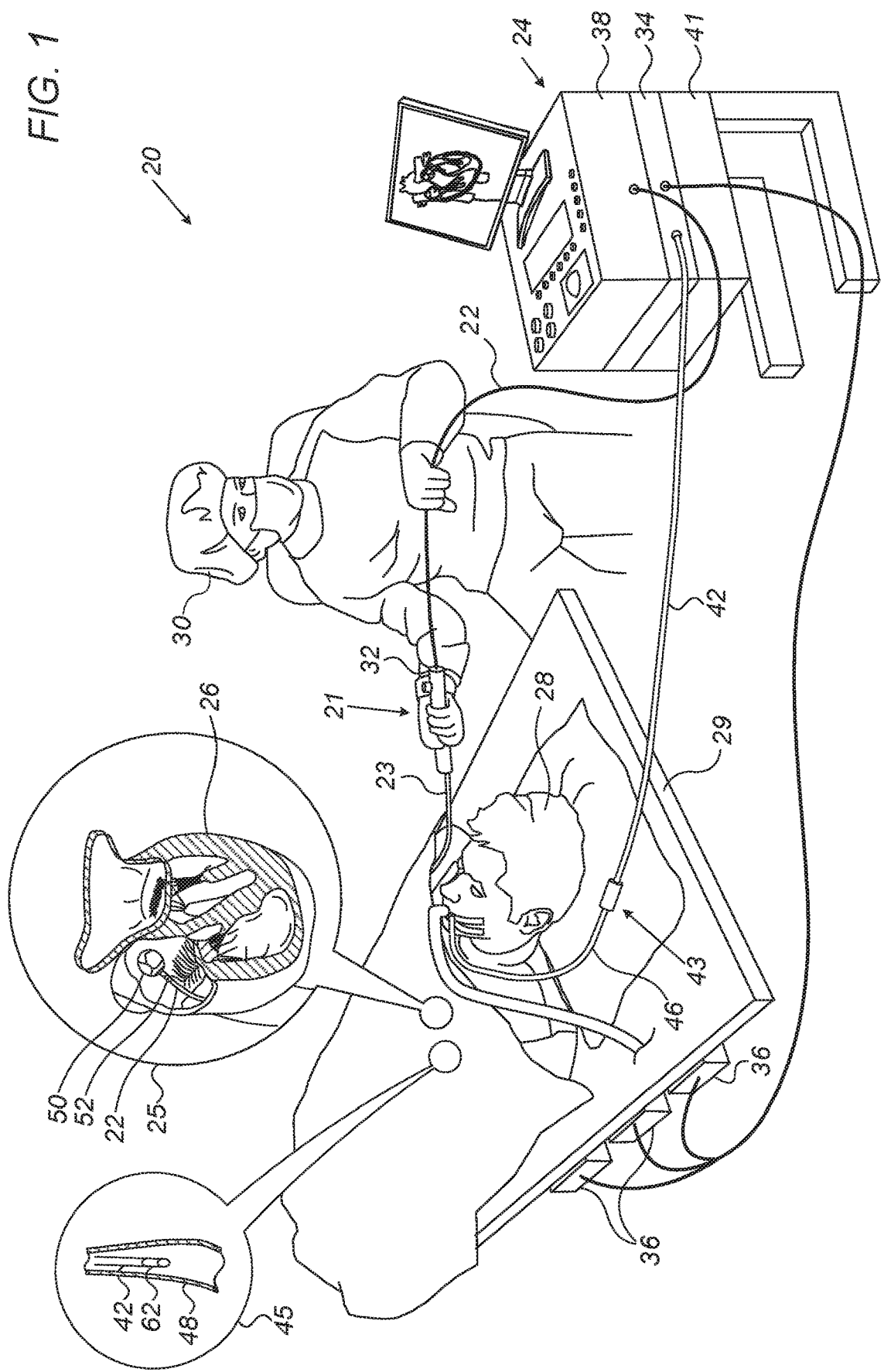
FIG. 1 is a schematic, pictorial illustration of a catheter-based position-tracking and ablation system, in accordance with an embodiment of the present invention.

The anatomic relationship between the esophagus and the left atrium of the heart can cause problems in catheter ablation of target tissue in the left atrium, such as pulmonary vein isolation procedures that are used in treating atrial fibrillation. The esophagus lies posterior to the left atrium and leads a variable course relative to the left atrium, adjacent to the right or left pulmonary vein or the posterior wall of the heart. Hence, there is a risk of esophageal damage due to the high temperatures occurring when ablation is performed anywhere in the posterior left atrium.

To prevent this sort of damage, some practitioners use an esophageal probe fitted with temperature sensors to give an indication of heating of the esophagus. But in some cases, the indication may take some time, and may be too late to prevent damage.

Embodiments of the present invention that are described herein offer a solution to this problem in cases in which a radio-frequency (RF) ablation balloon catheter or other multi-electrode ablation catheter is used for the ablation, and the ablation parameters of individual electrodes can be controlled. The distance from the electrodes to the esophagus is measured, and the ablation parameters to the electrode(s) closest to the esophagus are limited, as explained below.

In the disclosed embodiments, an esophageal probe having a magnetic field generator, comprising one or more transmitting coils, for example, is inserted into the esophagus. One or more magnetic sensors, such as receiving coils, in the ablation catheter provide signals that are indicative of the distance between the catheter electrodes and the magnetic field generator.

Knowing these distances, the ablation system can, prior to ablation, provide automatic limits on the ablation parameters to the electrode or electrodes closest to the esophagus to avoid damage to the esophagus. Typical parameters that are limited comprise the level and/or duration of the RF power applied. In addition, the temperature of the nearest electrode or electrodes can be measured, and this temperature can also be used to control the ablation parameters.

Based on these principles, the embodiments of the present invention that are described hereinbelow provide improved treatment systems for use in ablation procedures, and specifically for preventing collateral damage to the esophagus when performing cardiac ablation.

In some embodiments, the distal end of a catheter is inserted into the left atrium of a patient's heart. The distal end of the catheter contains a magnetic sensor and one or more ablation electrodes, which are configured to apply electrical energy to ablate tissue in the left atrium.

The distal end of a monitoring probe is inserted into the esophagus, and positioned at a location approximately adjacent to the left atrium, where the esophagus wall tissue is considered to be at risk of collateral thermal damage from the cardiac ablation procedure. The distal end of the monitoring probe comprises a magnetic field generator.

The cardiac catheter and the monitoring probe are both coupled at their proximal ends to a console. The console drives the magnetic field generator in the monitoring probe to emit magnetic fields, and receives signals from the magnetic sensor in the catheter in response to the magnetic fields. Based on these signals, a processor in the console estimates respective distances between the ablation electrodes and the distal end of the monitoring probe. The processor controls the electrical energy applied by the electrodes responsively to the estimated distances.

In some embodiments, the processor is configured to estimate the orientation of the catheter distal end, based on the signals from the magnetic sensor, and to further estimate the respective distances between the electrodes and the probe distal end responsively to the estimated orientation.

In an embodiment, an inflated balloon, fitted at the distal end of a catheter, is used in performing the ablation treatment. The balloon comprises electrodes distributed around its outer surface. The processor is configured to identify which of the electrodes are closest to the esophagus tissue at risk based on the rotation angle of the inflated balloon, as indicated by the estimated orientation of the catheter distal end. The processor can then limit the ablation parameters applied to these specific electrodes, which are at the greatest risk of damaging the esophageal tissue, for example by limiting the level of electrical power and/or the duration of the application of the electrical energy to these electrodes.

In an embodiment, the catheter comprises temperature sensors in proximity to the electrodes. The processor reads the temperature of the sensors closest to the electrodes that were found to be closest to the esophagus and controls the ablation parameters accordingly.

The disclosed method of setting the ablation parameters based on the estimated distances between the electrodes and the esophagus wall tissue at risk has the advantage, inter alia, of facilitating early detection of risk due to overheating of the esophagus wall tissue. By contrast, as noted earlier, by the time a temperature sensor in the esophagus detects an excessive temperature, it may be too late to prevent damage.

System Description

FIG. 1 is a schematic, pictorial illustration of a catheter-based position-tracking and ablation system 20, in accordance with an embodiment of the present invention. System 20 comprises a catheter 21, having a distal end 22 that is navigated by a physician 30 into a heart 26 of a patient 28 via the vascular system. In the pictured example, physician 30 inserts catheter 21 through a sheath 23, while manipulating distal end 22 using a manipulator 32 near the proximal end of the catheter.

As shown in an inset 25, distal end 22 comprises a magnetic sensor 52 contained within the distal end and a balloon 50. (The balloon is inserted through sheath 23 in a deflated state and is then inflated within heart 26.) In the embodiments described herein, catheter 21 is used for ablation of tissue in heart 26. Although the pictured embodiment relates specifically to the use of a balloon catheter for ablation of heart tissue, the elements of system 20 and the methods described herein may alternatively be applied in controlling ablation using other sorts of multi-electrode catheters, such as lasso, basket, and multi-arm catheters.

System 20 also comprises a monitoring probe 43, having a distal end 42 that is inserted into an esophagus 48 of patient 28 through a sheath 46. As seen in an inset 45, probe distal end 42 contains a magnetic field generator 62. In the embodiments described herein, monitoring probe 43 is used for estimating distances between the wall tissues of esophagus 48 and the electrodes on inflated balloon 50. Magnetic field generator 62 may also operate as a sensor in order to obtain positions of probe distal end 42 in the coordinate system of an external position tracking system, as described below.

The proximal ends of catheter 21 and monitoring probe are connected to a control console 24. Console 24 comprises a processor 41, typically a general-purpose computer, with suitable front end and interface circuits 38 for receiving signals from catheter 21, as well as for applying energy via catheter 21 to ablate tissue in heart 26 and for controlling the other components of system 20. Console 24 also comprises a driver circuit 34, configured to drive magnetic field generator 62.

During the insertion of catheter distal end 22, balloon 50 is maintained in a collapsed configuration. Once catheter distal end 22 has reached the target location within heart 26, physician 30 inflates balloon 50. Processor 41 in console 24 receives signals from magnetic sensor 52 in response to magnetic fields produced by magnetic field generator 62, and estimates the distances between the different ablation electrodes and the esophagus wall tissue at risk. Processor 41 then sets respective ablation parameters for one or more of the electrodes, and applies ablation energies to the tissue at the target ablation sites locations accordingly.

In some embodiments, magnetic sensor 52 also generates position signals in response to magnetic fields from external field generators 36, for example, for the purpose of measuring the position of balloon 50 in the heart cavity. Magnetic field generators 36 are placed at known positions external to patient 28, e.g., below a table 29 on which the patient is lying. These position signals are indicative of the position of inflated balloon 50 in the coordinate system of the position tracking system. Processor 41 may also receive signals output from magnetic field generator 62 in response to the fields of magnetic field generators 36, and may thus derive the position coordinates of distal end 42 of monitoring probe 43 in esophagus 48, as well.

This method of position sensing using external magnetic fields is implemented in various medical applications, for example, in the CARTO™ system, produced by Biosense Webster Inc. (Diamond Bar, Calif.) and is described in detail in U.S. Pat. Nos. 5,391,199, 6,690,963, 6,484,118, 6,239,724, 6,618,612 and 6,332,089, in PCT Patent Publication WO 96/05768, and in U.S. Patent Application Publications 2002/0065455 A1, 2003/0120150 A1 and 2004/0068178 A1, whose disclosures are all incorporated herein by reference. Alternatively, the principles of the present invention may be implemented, mutatis mutandis, using other position sensing technologies that are known in the art, such as ultrasonic or impedance-based position sensing.

Processor 41 typically comprises a general-purpose computer, which is programmed in software to carry out the functions described herein. The software may be downloaded to the computer in electronic form, over a network, for example, or it may, alternatively or additionally, be provided and/or stored on non-transitory tangible media, such as magnetic, optical, or electronic memory.

Cardiac Ablation Using Esophageal Probe with Transmitting Coils

Figure 2:
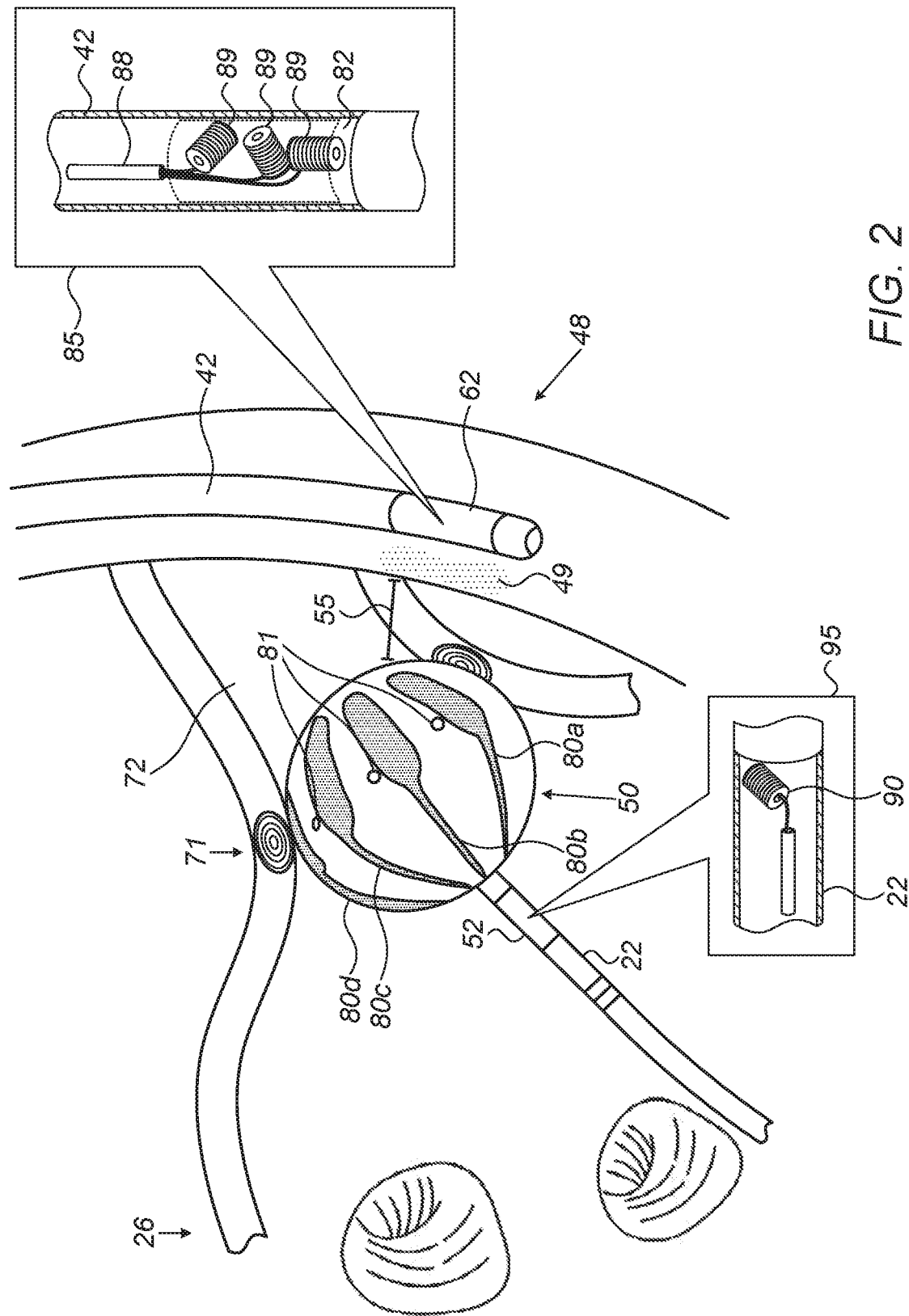
FIG. 2 is a schematic, pictorial illustration showing details of an esophageal probe and an inflated balloon positioned at an ostium of a pulmonary vein, in accordance with an embodiment of the present invention.

FIG. 2 is a schematic, pictorial illustration showing details of distal end 42 of monitoring probe 43 and inflated balloon 50, positioned at an ostium 71 of a pulmonary vein 72 in the left atrium of heart 26, in accordance with an embodiment of the present invention. Balloon 50 comprises multiple electrodes 80 that are distributed around its outer surface. Electrodes 80 that are visible in FIG. 2 are labeled as electrodes 80a-80d. As seen in the figure, electrode 80a faces toward and is the nearest to the wall of esophagus 48. Balloon 50 also comprises temperature sensors 81, wherein each temperature sensor 81 is in proximity to an electrode 80.

As shown in FIG. 2, distal end 42 of monitoring probe 43 is placed in esophagus 48 in proximity to esophageal wall tissue 49 that is at risk. Magnetic field generator 62 is contained within the probe distal end, as noted above.

In this embodiment, magnetic field generator 62 comprises at least one tri-axial transmitting coil assembly 82, as seen in an inset 85. Tri-axial coil assembly 82 comprises three transmitting coils 89, which are oriented along respective, mutually orthogonal axes. Each individual transmitting coil 89 is integrated with wiring 88 running through monitoring probe 43 to connect with console 24.

Magnetic sensor 52 comprises one or more sensing coils 90, as seen in an inset 95. It is desirable at least one such sensing coil be oriented perpendicular to the long axis of catheter distal end 22. Thus, the signal from coil 90 can be processed by processor 41 to find the angle of orientation of catheter distal end 22 relative to probe distal end 42, and specifically the angle of rotation about the catheter axis. Processor 41 is thus able to determine which of electrodes 80 is closest to esophagus 48 based on the measured angle of rotation and the known orientations of electrodes 80 with respect to the long axis of catheter distal end 22.

Esophageal wall tissue 49 at risk comprises a segment of the esophageal wall facing toward the posterior side of ostium 71. Based on the estimated orientation of electrodes 80 with respect to catheter distal end 22, and based on the largely known spatial relationship of the anatomy of esophagus 48 and that of ostium 71, processor 41 identifies the electrodes facing the segment of the esophagus tissue at risk and estimates their respective distances from tissue at risk 49. Specifically, in the present example, electrode 80a is identified as the nearest to tissue 49 at risk. Based on the signals from sensing coil 90, processor 41 estimates a distance 55 between electrode 80a and esophageal wall tissue 49 at risk. Processor 41 then sets the ablation parameters of the electrodes according to the principles described above, and specifically limits at least one of the level of electrical power and the duration of the application of the electrical energy by electrode 80a.

Additionally or alternatively, processor 41 can control the ablation parameters applied to electrode 80a based on the temperature indicated by one or more of temperature sensors 81 in proximity to electrode 80a.

The example configuration shown in FIG. 2 is chosen purely for the sake of conceptual clarity. The disclosed techniques may similarly be applied using system components and settings. For example, system 20 may comprise other sorts of ablation devices, such as a circular multi-electrode catheter (e.g., the Lasso® catheter made by Biosense Webster Inc.) or a multi-branch multi-electrode catheter (e.g., PentaRay® made by Biosense Webster Inc.).

As another example, the disclosed treatment method may utilize devices based on laser ablative power, such as a laser ablation balloon that is fitted to the catheter distal end. The laser aiming points on the target tissue coincide with the balloon outer surface that is positioned in physical contact with the tissue. The different distances between the laser aiming points and the esophageal tissue at risk are estimated using the same method described above. Then, at least one of the level of laser power and duration of laser ablation are set to avoid causing collateral thermal damage.

Figure 3:
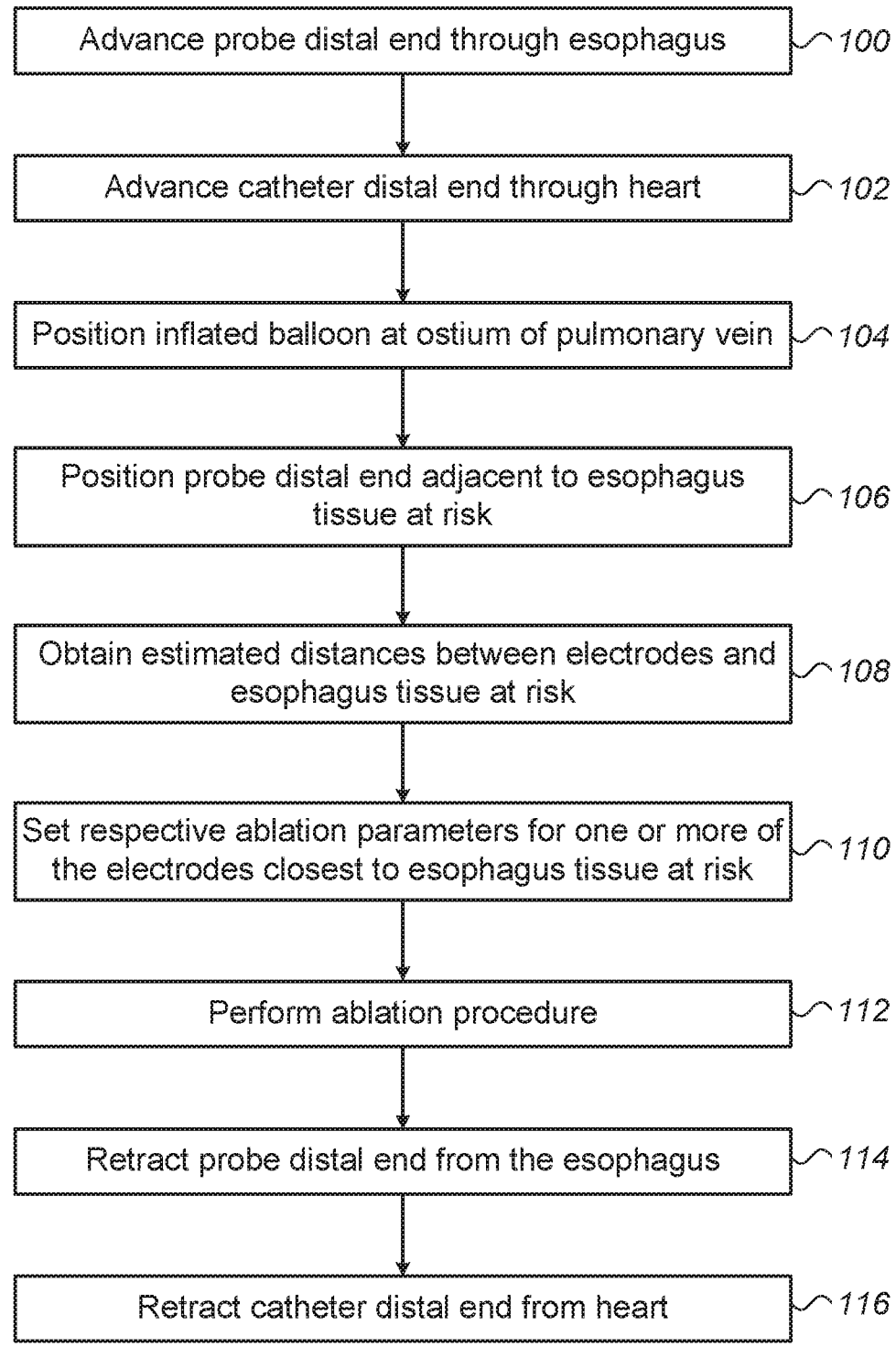
FIG. 3 is a flow chart that schematically illustrates a method for performing an ablation procedure, in accordance with an embodiment of the present invention.

FIG. 3 is a flow chart that schematically illustrates a medical procedure involving ablation of tissue around ostium 71 of pulmonary vein 72, in accordance with an embodiment of the present invention. The procedure begins with physician 30 advancing probe distal end 42 through the esophagus, at a probe advancement step 100.

Physician 30 then advances catheter distal end 22 to the heart, at a catheter advancement step 102.

At a balloon positioning step 104, physician 30 positions inflated balloon 50 at the target ostium 71 of pulmonary vein 72.

At a probe positioning step 106, physician 30 positions probe distal end 42 adjacent to tissue 49 at risk in the esophageal wall.

At a distance estimation step 108, processor 41 actuates magnetic field generator 62 and receives corresponding signals from sensing coil 90. Processor 41 analyzes these signals in order to estimate the respective distances of electrodes 80 from esophageal tissue 49 at risk.

At an ablation parameter setting step 110, physician 30 sets the ablation parameters for ablation procedure. Processor 41 automatically limits the ablation power and/or time for one or more of electrodes 80 closest to esophageal tissue 49, for example electrode 80a in FIG. 2.

At a treatment step 112, physician 30 instructs processor 41 to apply the required ablation energy. The processor monitors the ablation parameters and/or the temperature of electrodes 80 that are closest to esophageal tissue 49 to ensure that they do not exceed the limits set at step 110.

Upon completion of the procedure, at a retraction step 114, physician 30 retracts catheter distal end 22 from the heart.

At a retraction step 116, physician 30 also retracts probe distal end 42 from the esophagus.

The example flow chart shown in FIG. 3 is shown here purely for the sake of conceptual clarity. In alternative embodiments, the disclosed technique may use different and/or additional steps, such for example monitoring each electrode temperature using the corresponding temperature sensor 81 and modifying treatment accordingly.

Although the embodiments shown in the figures relate to a specific organ and type of treatment, the principles of the invention may be applied in preventing collateral damage to nearby organs in other sorts of invasive procedures, such as for example, needle localization, wherein the needle may be used for injecting an implant or for taking a biopsy. In an embodiment, a needle is fitted to catheter distal end 22. In another embodiment, a biopsy tool is fitted to catheter distal end 22. In an embodiment, catheter distal end 22 comprises sensing electrodes for acquiring electrograms. In another embodiment, distal end of monitoring probe 43 also includes an ultrasound transducer. The ultrasound transducer may be configured to generate and detect echo signals, and transmit the detected signals for analysis by processor 41, which is coupled to drive the ultrasound transducer and to analyze the detected echo signals, as to corroborate measurements results obtained using the magnetic sensor and/or to provide additional measurements related to the catheter distal end 22, such as a position of a needle or a biopsy tool fitted at catheter distal end 22.

It will be appreciated that the embodiments described above are cited by way of example, and that the present invention is not limited to what has been particularly shown and described hereinabove. Rather, the scope of the present invention includes both combinations and sub-combinations of the various features described hereinabove, as well as variations and modifications thereof which would occur to persons skilled in the art upon reading the foregoing description and which are not disclosed in the prior art. Documents incorporated by reference in the present patent application are to be considered an integral part of the application except that to the extent any terms are defined in these incorporated documents in a manner that conflicts with the definitions made explicitly or implicitly in the present specification, only the definitions in the present specification should be considered.

The invention claimed is:

1. A system for cardiac treatment, comprising:
a monitoring probe having a probe distal end configured for insertion into an esophagus of a patient, and a magnetic field generator coupled to the probe distal end;
a catheter having a catheter distal end configured for insertion into a heart of the patient and comprising a magnetic sensor coupled to the catheter distal end; and
a console, which is configured to drive the magnetic field generator to emit magnetic fields, to receive signals from the magnetic sensor in response to the magnetic fields, and to estimate respective distances between the catheter distal end and the probe distal end based on the signals;
the system further comprising one or more electrodes disposed on the catheter distal end and disposed at respective locations around the catheter distal end;
wherein the console is configured to estimate an orientation and a rotation angle of the catheter distal end based on the signals, and to estimate the respective distances between each of the electrodes and the probe distal end responsively to the estimated orientation and rotation angle;
wherein the console is further configured to identify one or more electrodes facing esophagus tissue at risk of collateral thermal damage, and to estimate their respective distances from the tissue at risk, and to set the ablation parameters of the one or more electrodes facing the tissue at risk, to limit at least one of a level of electrical power and a duration of application of electrical energy in response to the respective distances from the tissue at risk before a temperature sensor in the esophagus detects an excessive temperature.

2. The system according to claim 1, wherein the one or more electrodes are configured to apply electrical energy to ablate tissue in the heart.

3. The system according to claim 2, wherein the console is configured to set different, respective ablation parameters for application of the electrical energy to the electrodes, responsively to the distances between one or more of the electrodes and the probe distal end.

4. The system according to claim 3, wherein the ablation parameters comprise at least one of a level of electrical power and a duration of the application of the electrical energy.

5. The system according to claim 1, wherein the catheter distal end comprises a balloon, which is inflatable within the heart, wherein the one or more electrodes comprise multiple electrodes that are distributed around an outer surface of the balloon, and wherein the console is configured to identify one of the electrodes that is closest to the esophagus responsively to a rotation angle of the balloon, which is indicated by the estimated orientation.

6. The system according to claim 5, wherein the console is configured to limit an energy of ablation that is applied to the identified one of the electrodes.

7. The system according to claim 5, wherein the catheter comprises temperature sensors mounted in proximity to the electrodes, and wherein the console is configured to control one or more ablation parameters responsively to a temperature indicated by one or more of the temperature sensors in proximity to the identified one of the electrodes.

8. The system according to claim 1, and comprising a needle, which is mounted on the catheter distal end and is configured to inject fluid or an implant.

9. The system according to claim 1, and comprising a biopsy tool, which is mounted on the catheter distal end and is configured to perform a biopsy.

10. The system according to claim 1, wherein the monitoring probe comprises an ultrasound transducer configured to generate and detect echo signals.

11. A method for cardiac treatment, comprising:
inserting a monitoring probe, comprising a probe distal end having a magnetic field generator coupled thereto, into an esophagus of a patient;
inserting a catheter, comprising a catheter distal end having a magnetic sensor coupled thereto and one or more electrodes disposed on the catheter distal end and disposed at respective locations around the catheter distal end, into a heart of the patient;
driving the magnetic field generator to emit magnetic fields while the probe distal end is in the esophagus;
estimating an orientation and a rotation angle of the catheter distal end based on signals received from the magnetic sensor in response to the magnetic fields; and
estimating respective distances between each of the one or more of the electrodes and the probe distal end based on signals received from the magnetic sensor in response to the estimated orientation and rotation angle and the magnetic fields while the catheter distal end is in the heart;
identifying one or more electrodes facing esophagus tissue at risk of collateral thermal damage, and estimating their respective distances from the tissue at risk;
setting the ablation parameters of the one or more electrodes facing the tissue at risk, to limit at least one of a level of electrical power and a duration of application of electrical energy in response to the respective distances from the tissue at risk before a temperature sensor in the esophagus detects an excessive temperature.

12. The method according to claim 11, and comprising applying electrical energy to ablate tissue in the heart using the one or more electrodes.

13. The method according to claim 12, wherein applying the electrical energy comprises setting different, respective ablation parameters for application of the electrical energy to the electrodes, responsively to the distances.

14. The method according to claim 13, wherein setting the ablation parameters comprises setting at least one of a level of electrical power and a duration of the application of the electrical energy.

15. The method according to claim 11, wherein the one or more electrodes comprise multiple electrodes that are distributed around an outer surface of a balloon, and comprising identifying one of the electrodes that is closest to the esophagus, responsively to a rotation angle of the balloon, which is indicated by the estimated orientation.

16. The method according to claim 15, and comprising limiting an energy of ablation that is applied to the identified one of the electrodes.

17. The method according to claim 15, and comprising controlling one or more ablation parameters responsively to a temperature indicated by one or more temperature sensors in proximity to the identified one of the electrodes.

18. The method according to claim 11, and comprising injecting fluid or an implant using a needle that is mounted on the catheter distal end.

19. The method according to claim 11, and comprising performing a biopsy using a biopsy tool that is mounted on the catheter distal end.

20. The method according to claim 11, and comprising generating and detecting echo signals using an ultrasound transducer that is fitted at the probe distal end.

* * * * *